(12) United States Patent
Ito

(10) Patent No.: US 7,858,114 B2
(45) Date of Patent: Dec. 28, 2010

(54) PERCUTANEOUS ABSORPTION PREPARATIONS OF ANTIDEMENTIA DRUGS

(75) Inventor: Takeshi Ito, Fukuoka (JP)

(73) Assignee: Teikoku Seiyaku Co., Ltd., Kagawa (JP)

( * ) Notice: Subject to any disclaimer, the term of this patent is extended or adjusted under 35 U.S.C. 154(b) by 364 days.

(21) Appl. No.: 11/797,722

(22) Filed: May 7, 2007

(65) Prior Publication Data

US 2007/0259028 A1 Nov. 8, 2007

Related U.S. Application Data

(60) Provisional application No. 60/798,296, filed on May 8, 2006.

(51) Int. Cl.
*A61K 31/55* (2006.01)
*A61K 31/473* (2006.01)
*A61K 31/445* (2006.01)
*A61K 31/13* (2006.01)

(52) U.S. Cl. .................. 424/449; 424/443; 424/448; 514/214.01; 514/297; 514/319; 514/663; 514/946; 514/947

(58) Field of Classification Search .......... 424/426, 424/449, 465, 486; 514/11, 28, 332, 449, 514/509
See application file for complete search history.

(56) References Cited

U.S. PATENT DOCUMENTS

| 2004/0028724 A1* | 2/2004 | Terahara et al. ............ 424/449 |
| 2004/0086552 A1* | 5/2004 | Klokkers et al. ............ 424/449 |
| 2004/0258741 A1* | 12/2004 | Terahara et al. ............ 424/449 |

FOREIGN PATENT DOCUMENTS

| JP | 04-117323 | 4/1992 |
| JP | 6-199659 | 7/1994 |
| JP | 10-182439 | 7/1998 |
| JP | 11-315016 | 11/1999 |
| JP | 2005-194230 | 7/2005 |
| WO | 91/03998 | 4/1991 |
| WO | 93/03692 | 4/1993 |
| WO | 96/10429 | 4/1996 |
| WO | 01/07017 | 2/2001 |
| WO | 02/26216 | 4/2002 |
| WO | 02/38139 | 5/2002 |
| WO | 02-45699 | 6/2002 |
| WO | 03/032960 | 4/2003 |
| WO | 03/092677 | 11/2003 |
| WO | 2005/115355 | 12/2005 |

OTHER PUBLICATIONS

International Search Report issued Mar. 26, 2007 in International (PCT) Application No. PCT/JP2006/325813.

* cited by examiner

*Primary Examiner*—Johann R Richter
*Assistant Examiner*—Hong Yu
(74) *Attorney, Agent, or Firm*—Wenderoth, Lind, & Ponack, L.L.P.

(57) ABSTRACT

Disclosed is a percutaneous absorption preparation which enables the stable administration of an antidementia drug over a long period of time. More particularly, the percutaneous absorption preparation of the antidementia drug which is used as a plaster on skin comprises at least an adherent layer, an intermediate membrane, and a drug reservoir layer sequentially from the side which is plastered on skin, wherein the drug reservoir layer comprises at least an antidementia drug, an aminated polymer, a polyhydric alcohol, and one or more carboxylic acid esters, the intermediate membrane enables the controlled permeation of the antidementia drug into the side of skin, the adherent layer enables the plastering of the percutaneous absorption preparation on skin, and is permeable to the antidementia drug.

8 Claims, 2 Drawing Sheets

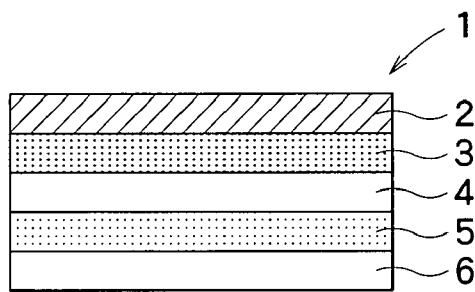
F I G. 1
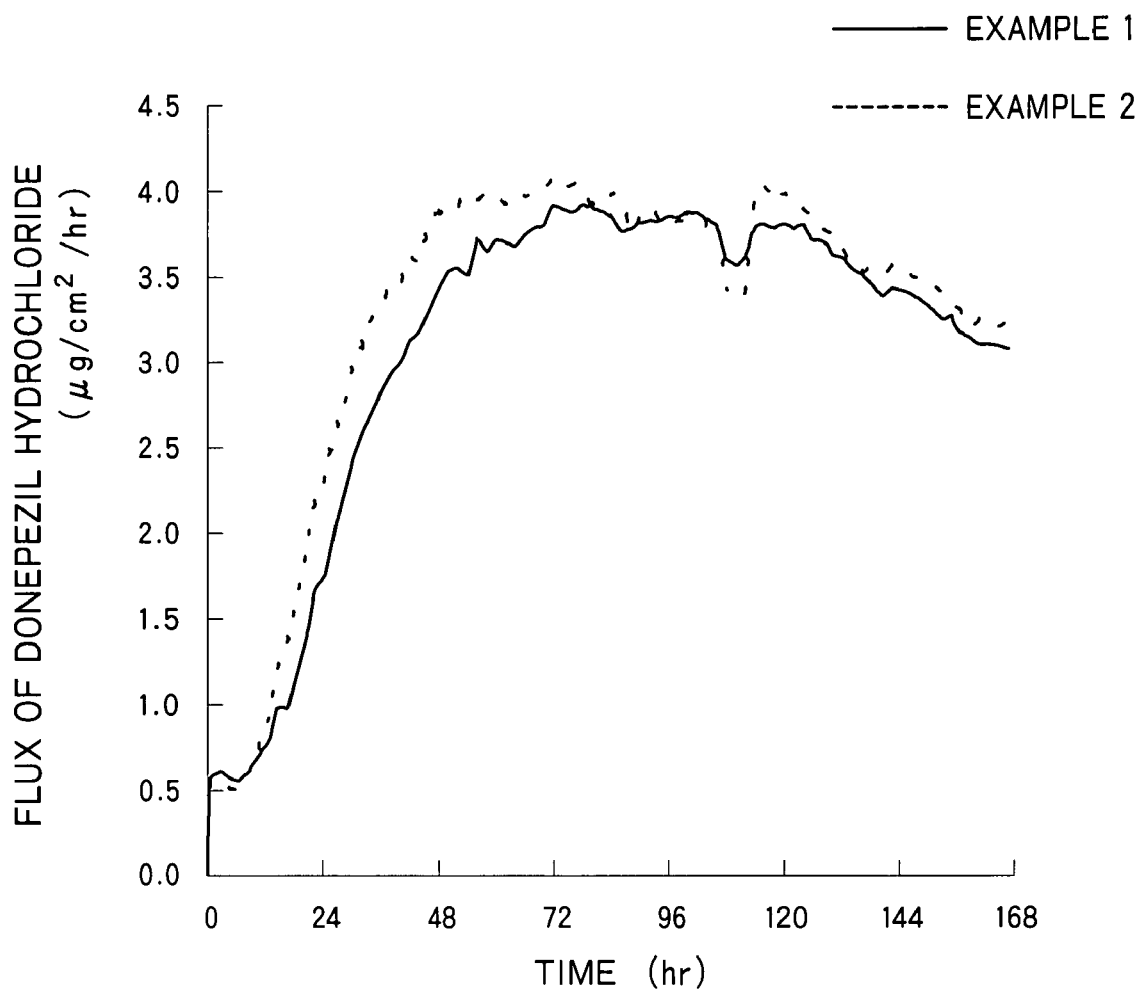
F I G. 2

PERCUTANEOUS ABSORPTION PREPARATIONS OF ANTIDEMENTIA DRUGS

CROSS REFERENCE TO RELATED APPLICATIONS

This application claims priority to U.S. provisional application 60/798,296 filed on May 8, 2006, the entire disclosure of which is incorporated herein by reference.

BACKGROUND OF THE INVENTION

1. Field of the Invention

The present invention relates to a percutaneous absorption preparation which enables stable administration of an antidementia drug over a long period of time.

2. Background Art

Recently, dementia patients with Alzheimer's type have been increased with population growth of seniors, and the care of patients becomes a serious social problem. On the other hand, antidementia drugs have rapidly been developed, and for example donepezil hydrochloride has extensively been used as a remedy against Alzheimer's disease which has acetylcholinesterase inhibitory effect. Hitherto, these antidementia drugs have mostly been administered orally in the form of tablets. Drugs are administered to patients in the form of tablets, capsules, syrups, granules as well as via injection, rectal dosage, and the like, which are appropriately chosen depending on diseases or the property of the drugs.

However, it is often hard for a dementia patient in an advanced stage to take an antidementia drug. Therefore, the transdermal administration of the antidementia drug is believed very useful in administering the drug continuously for a long period without difficulty in taking the drug.

However, it is generally considered that poor permeability of a drug to skin leads to the difficulty of absorbing the drug in an amount sufficient to exert effect into body through the skin. Percutaneous absorption preparations for antidementia drugs have hitherto been examined in order to get over the difficulty.

For example, Japanese Patent Laid-Open Publication No. 1998/315016 (JP 11-315016A) discloses an ointment for the percutaneous administration of antidementia drug or a suppository for the rectal administration of the drug and it is reported that the percutaneous absorbability of donepezil is enhanced with use of base material containing a higher alcohol and an ester derivative thereof.

Further, WO 03/032960 discloses a percutaneous absorption preparation for the treatment of dementia, the preparation comprising an adhesive composition, the adhesive composition containing an active ingredient dispersed therein, the active ingredient being released at a pharmacologically effective rate, and the skin permeation rate thereof being 1.2 $\mu g/cm^2$/hour or more. In addition, Example discloses an adhesive composition containing preparation which comprises a donepezil hydrochloride as the active ingredient, a styrene-isoprene-styrene block copolymer as the hydrophobic polymer, and sodium acetate as the organic acid salt, and the size of the preparation for a single dosage for 24 hours is regarded as 60 $cm^2$.

Furthermore, it is required for a percutaneous absorption preparation that the drug as the active ingredient is maintained without deposition in the preparation and placed stably on the skin. Thus, the percutaneous absorption preparation and its materials have been examined in consideration of the improvement of these functions.

For example, Japanese Patent Laid-Open Publication No. 1998/182439 (JP 10-182439A) discloses an adhering and joining agent for skin or transdermal treatment systems, which comprises a (meth)acrylate copolymer containing a tertiary or quaternary amino group, an acidic group-containing acrylate or (meth)acrylate polymer or copolymer, and a plasticizer. Example of the publication discloses triethyl citrate and acetyl triethyl citrate as the plasticizer.

Also, WO 02/38139 discloses a percutaneous absorption preparation comprising an aminated polymer, a drug in the form of an acid addition salt, and a carboxylic acid and/or a salt thereof.

In addition, Japanese Patent Laid-Open Publication No. 1992/117323 (JP 04-117323A) discloses a percutaneous absorption preparation which maintains a adhesive layer containing a drug on a backing layer, characterized in that the percutaneous absorption preparation contains a certain amount of a drug in the form of an acid addition salt and a polymer containing a certain amount of a basic nitrogen and having no tackiness to skin at ordinary temperature.

However, when the antidementia drug is intended to administer to a patient for a long period, for example one week or so, it is still difficult to stably hold the preparation on the skin and continuously release the antidementia drug from the preparation. Thus, it can be said that a percutaneous absorption preparation of an antidementia drug which has both stable drug releasability and adhering ability to skin suitable for the administration of the drug for a long period is still needed.

SUMMARY OF THE INVENTION

The present inventors have now established a novel percutaneous absorption preparation provided with both stable drug releasability and adhering ability to skin suitable for the administration of a drug for a long period.

The present invention is based on such information.

Thus, the object of the present invention is to provide a novel percutaneous absorption preparation provided with both stable drug releasability and adhering ability to skin suitable for the administration of a drug for a long period.

And the percutaneous absorption preparation of an antidementia drug according to the present invention which is used as a plaster on skin comprises at least an adherent layer, an intermediate membrane, and a drug reservoir layer sequentially from the side which is plastered on skin, wherein said drug reservoir layer comprises at least an antidementia drug, an aminated polymer, a polyhydric alcohol, and one or more carboxylic acid esters, said intermediate membrane enables the controlled permeation of the antidementia drug into the side of skin, said adherent layer enables the plastering of the percutaneous absorption preparation to skin and is permeable to the antidementia drug.

According to the percutaneous absorption preparation of the present invention, it becomes possible to stably release the antidementia drug from the preparation over a long period and stably hold the preparation on the skin during the period of administering the drug. Thus, the percutaneous absorption preparation of the present invention can be advantageously used for continuously administering the antidementia drug for a long period.

BRIEF DESCRIPTION OF THE DRAWINGS

FIG. 1 is a sectional view which shows an embodiment of the percutaneous absorption preparation according to the present invention.

FIG. 2 is a graph which shows the result of the in vitro permeation test of the percutaneous absorption preparation according to the present invention through human skin.

DETAILED DESCRIPTION OF THE INVENTION

Definition

Figure 3:
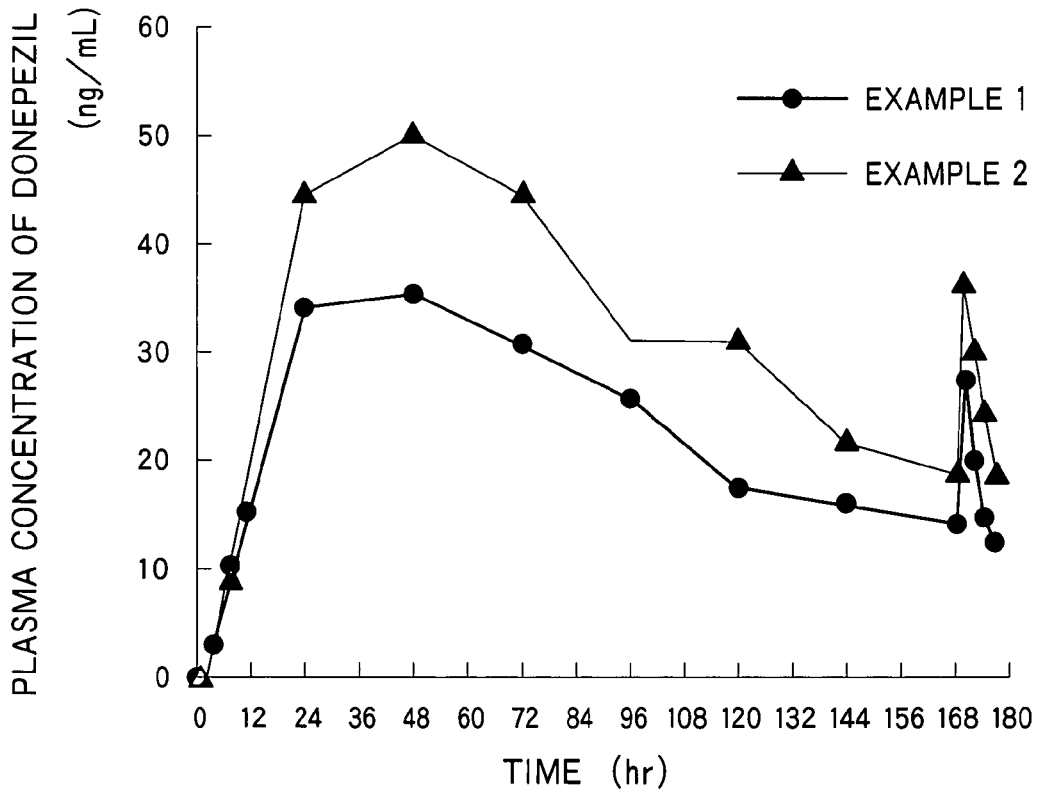
FIG. 3 is a graph which shows the concentration of the antidementia drug in rabbit plasma in a single dosage of the percutaneous absorption preparation according to the present invention.

The term "alkyl" as used herein means a linear, branched or cyclic alkyl, preferably a linear alkyl.

Also, the expression such as "C10" in a group or a part of a group means that "the total number of carbon is 10" in the group or a part of the group. Thus, "sebacic acid ($HO_2C(CH_2)_8CO_2H$)" as an example is included in the "C10 carboxylic acid".

Percutaneous Absorption Preparation

The percutaneous absorption preparation according to the present invention is, as described above, composed of a drug reservoir layer having a specific composition, an intermediate membrane, and an adherent layer.

Drug Reservoir Layer

The drug reservoir layer of the present invention comprises at least an antidementia drug, an aminated polymer, a polyhydric alcohol, and one or more carboxylic acid esters. The drug reservoir layer having such composition can stably maintain the antidementia drug at high doses required for its administration for a long period. Furthermore, according to the drug reservoir layer, it is possible to sustain the excellent drug releasability for a long period. Thus, the drug reservoir layer can be advantageously used for the administration of the antidementia drug for a long period.

According to the preferred embodiment of the present invention, a permeation rate through the skin (flux) can be improved when the antidementia drug is a basic drug. Such an excellent effect has not been elucidated as yet, it can be indicated as the reason of the effect that the basic drug is reacted with the aminated polymer resulting in desalting and forming a free base advantageous to the percutaneous absorption of the drug. According to the more preferred embodiment of the present invention, the basic drug is a nitrogen-containing basic drug or a salt thereof, and the salt is a pharmacologically acceptable one and includes without limited to, for example, hydrochloride, tartrate, hydrobromide, and the like.

Moreover, the basic drug or a salt thereof described above is preferably donepezil hydrochloride, memantine hydrochloride, rivastigmine tartrate, galantamine hydrobromide, or tacrine hydrochloride, more preferably donepezil hydrochloride.

Also, the content of the antidementia drug in the drug reservoir layer can be made in the range of 0.5-50% by weight, preferably in the range of 10-40% by weight, and more preferably in the range of 15-35% by weight in consideration of the administration for a long period. Thus, the drug reservoir layer capable of containing the drug even in a high dose is advantageous to the production of a percutaneous absorption preparation having a size suitable for practical use.

Moreover, the aminated polymer in the drug reservoir layer is a copolymer which is preferably composed of a dialkylaminoalkyl(meth)acrylate and a monomer unit selected from an alkyl(meth)acrylate, a hydroxyalkyl(meth)acrylate and a combination thereof. The copolymer is advantageous to the stable maintenance of the drug and the realization of a good flux of the drug.

In addition, the dialkylaminoalkyl(meth)acrylate is preferably a di-C1-4 alkylamino C1-12 alkyl(meth)acrylate, and more preferably a di-C1-2 alkylamino C1-2 alkyl(meth)acrylate. More specifically, the dialkylaminoalkyl(meth)acrylate includes dimethylaminomethyl(meth)acrylate, diethylaminomethyl (meth)acrylate, dimethylaminoethyl(meth)acrylate, dimethylaminobutyl(meth)acrylate, diethylaminooctyl (meth)acrylate, and the like.

Furthermore, the monomer units other than the dialkylaminoalkyl(meth)acrylate in the copolymer is an alkyl (meth)acrylate or a hydroxyalkyl(meth)acrylate, more preferably a C1-12 alkyl(meth)acrylate or a monohydroxy C2-4 alkyl (meth)acrylate, and more preferably a C1-4 alkyl(meth)acrylate or a monohydroxy C2-4 alkyl(meth)acrylate. More specifically, the monomer unit includes methyl(meth)acrylate, ethyl (meth)acrylate, propyl(meth)acrylate, butyl(meth)acrylate, octyl (meth)acrylate, 2-hydroxyethyl(meth)acrylate, 2-ethylhexyl (meth)acrylate, dodecyl(meth)acrylate, and the like.

Moreover, the aminated polymer is preferably a copolymer which is composed of a di-C1-2 alkylamino C1-2 alkyl (meth)acrylate and a monomer unit selected from a C1-4 alkyl (meth)acrylate, a monohydroxy C2-4 alkyl (meth)acrylate and a combination thereof, more preferably a methyl (meth)acrylate-butyl (meth)acrylate-dimethylaminoethyl (meth)acrylate copolymer, and further preferably a methyl methacrylate-butyl methacrylate-dimethylaminoethyl methacrylate copolymer. Such methyl methacrylate-butyl methacrylate-dimethylaminoethyl methacrylate copolymer is commercially available, for example, as EUDRAGIT® E100 (Degussa).

Also, the physical properties such as the molar ratio of the monomer units or molecular weights in the aminated polymer described above may be appropriately controlled by those skilled in the art.

Furthermore, the content of the aminated polymer in the drug reservoir layer is preferably in the range of 5-30% by weight, more preferably 10-25% by weight.

In addition, the carboxylic acid ester in the drug reservoir layer of the present invention is preferably selected from an ester of a polyvalent carboxylic acid and a monohydroxy alcohol, an ester of a fatty acid and a polyhydric alcohol, and a combination thereof, and more preferably a combination of an ester of a polyvalent carboxylic acid and a monohydroxy alcohol and an ester of a fatty acid and a polyhydric alcohol.

The addition of the ester of the polyvalent carboxylic acid and the monohydroxy alcohol described above to the drug reservoir layer is preferred for controlling the plasticity of the drug reservoir layer.

The polyvalent carboxylic acid in the ester described above is preferably di- or tri-valent. Moreover, the polyvalent carboxylic acid is preferably of C6-10.

The monohydroxy alcohol in the ester described above is preferably of C2-4.

More specifically, the ester of the polyvalent carboxylic acid and the monohydroxy alcohol is preferably an alkyl citrate ester and/or an alkyl sebacate ester, more preferably a C2-4 alkyl citrate and/or a C2-4 alkyl sebacate, more preferably a tri-(C2-4)-alkyl citrate and/or a di-(C2-4)-alkyl sebacate, more preferably triethyl citrate and/or diethyl sebacate.

Also, the addition of the ester of the fatty acid and the polyhydric alcohol described above to the drug reservoir layer is advantageous to the enhancement of the percutaneous absorption of the drug.

Furthermore, the ester of the fatty and the polyhydric alcohol described above is preferably at least the one selected from the group consisting of a sorbitan fatty acid ester, a propylene glycol fatty acid ester and a glycerin fatty acid ester, more preferably a sorbitan fatty acid ester, further preferably a sorbitan C7-19 fatty acid ester. Specific examples of the sorbitan fatty acid ester include sorbitan monolaurate, sorbitan monostearate, sorbitan monoleate, sorbitan monopalmitate, sorbitan trioleate, and sorbitan tristearate, preferably sorbitan monolaurate.

Also, the content of the carboxylic acid ester in the drug reservoir layer is preferably in the range of 3-20% by weight, more preferably 5-15% by weight.

In addition, when the ester of the polyvalent carboxylic acid and the monohydroxy alcohol is used, the content of the ester of the polyvalent carboxylic acid and the monohydroxy alcohol in the drug reservoir layer is preferably 3-15% by weight, more preferably 3-10% by weight.

Also, when the ester of the fatty acid and the polyhydric alcohol is used, the content of the ester of the fatty acid and the polyhydric alcohol in the drug reservoir layer is preferably 1-10% by weight, more preferably 2-5% by weight.

Furthermore, the polyhydric alcohol in the drug reservoir layer is preferably a sugar alcohol and/or a glycol, more preferably at least the one selected from the group consisting of tritol, pentitol, hexitol, and glycol. More specifically, the polyhydric alcohol is the one selected from glycerin, propylene glycol, dipropylene glycol, butylene glycol, d-sorbitol, xylitol, mannitol, polyethylene glycol, and a combination thereof, more preferably glycerin. The addition of the polyhydric alcohol described above to the drug reservoir layer is advantageous to the improvement of the stability of the antidementia drug.

Also, the content of the polyhydric alcohol in the drug reservoir layer is preferably in the range of 1-10% by weight, more preferably 3-10% by weight.

The drug reservoir layer of the present invention preferably contains further an acrylic polymer in consideration of its physicochemical stability.

The acrylic polymer is not particularly limited unless it disturbs the release and retainment of the drug, and preferably includes a (meth)acrylate-vinyl ester copolymer.

The (meth)acrylate which is a component of the acrylic polymer preferably includes an alkyl(meth)acrylate, a monohydroxyalkyl(meth)acrylate or an epoxyalkyl(meth)acrylate, more preferably a C1-12 alkyl(meth)acrylate, a monohydroxy C2-4 alkyl(meth)acrylate, or glycidyl(meth)acrylate. More specifically, the (meth)acrylate includes methyl(meth)acrylate, ethyl (meth)acrylate, propyl(meth)acrylate, butyl (meth)acrylate, octyl (meth)acrylate, hydroxyethyl(meth)acrylate, 2-ethylhexyl (meth)acrylate, dodecyl(meth)acrylate, glycidyl(meth)acrylate, and the like.

Also, the vinyl ester which is a component of the acrylic polymer includes vinyl acetate, vinyl propionate, vinyl butyrate, vinyl crotonate, vinyl caprate and the like, preferably vinyl acetate.

More specifically, the acrylic polymer described above is preferably a copolymer composed of a monomer unit selected from an alkyl (meth)acrylate, a monohydroxyalkyl (meth) acrylate, an epoxyalkyl (meth)acrylate, and a combination thereof, and vinyl acetate, more preferably a copolymer composed of a monomer unit selected from a C1-12 alkyl (meth) acrylate, a monohydroxy C2-4 alkyl (meth)acrylate, glycidyl (meth)acrylate, and a combination thereof, and vinyl acetate, more preferably, a copolymer composed of a monomer unit selected from 2-ethylhexyl (meth)acrylate, hydroxyethyl (meth)acrylate, glycidyl (meth)acrylate, and a combination thereof, and vinyl acetate, further preferably, a copolymer composed of a monomer unit selected from 2-ethylhexyl acrylate, hydroxyethyl acrylate, glycidyl methacrylate, and vinyl acetate. Specific examples of the acrylic polymer include DURO-TAK®387-2516, 87-2287, 87-4287(National Starch &Chemical Co., Ltd.), and the like.

Also, the physical properties such as the molar ratio of the monomer units or molecular weights of the aminated polymer described above may be controlled appropriately by those skilled in the art.

When the acrylic polymer is added to the drug reservoir layer, the content of the acrylic polymer is preferably in the range of 5-60% by weight, more preferably 15-50% by weight.

The drug reservoir layer of the present invention can be appropriately formed as far as the constituents are used in the amounts as described above.

Furthermore, according to the preferred embodiment of the present invention, the drug reservoir layer comprises a basic antidementia drug or a salt thereof, an aminated polymer, a polyhydric alcohol, an ester of the polyvalent carboxylic acid and the monohydroxy alcohol, an ester of the fatty acid and the polyhydric alcohol, and an acrylic polymer.

In addition, according to the more preferred embodiment of the present invention, the drug reservoir layer comprises a basic antidementia drug or a salt thereof, a methyl (meth)acrylate-butyl(meth)acrylate-dimethylaminoethyl (meth) acrylate copolymer; a sugar alcohol and/or a glycol; a C2-4 alkyl citrate and/or a C2-4 alkyl sebacate; a sorbitan fatty acid ester; and a (meth)acrylate-vinyl ester copolymer.

Also, according to the more preferred embodiment of the present invention, the drug reservoir layer comprises a basic antidementia drug or a salt thereof, a methyl(meth)acrylate-butyl (meth)acrylate-dimethylaminoethyl(meth)acrylate copolymer; a sugar alcohol and/or a glycol; a C2-4 alkyl citrate and/or a C2-4 alkyl sebacate; a sorbitan C7-19 fatty acid ester; and a copolymer composed of a monomer unit selected from a alkyl(meth)acrylate, a monohydroxyalkyl(meth)acrylate, an epoxyalkyl(meth)acrylate and a combination thereof, and a vinyl actate.

Also, according to the more preferred embodiment of the present invention, the drug reservoir layer comprises a basic antidementia drug or a salt thereof; a methyl methacrylate-butyl methacrylate-dimethylaminoethyl methacrylate copolymer; at least one polyhydric alcohol selected from the group consisting of glycerin, propylene glycol, dipropylene glycol, butylene glycol, d-sorbitol, xylitol, mannitol and polyethylene glycol; a tri-(C2-4)-alkyl citrate and/or a di-(C2-4)-alkyl sebacate; sorbitan C7-19 fatty acid ester; and a copolymer composed of a monomer unit consisting of 2-ethylhexyl acrylate, hydroxyethyl acrylate and glycidyl methacrylate and vinyl acetate.

Also, the thickness of the drug reservoir layer according to the present invention is appropriately determined by those skilled in the art in consideration of the factors such as the amount of the drug, and can be made in the range of 50-150 µm. In addition, the drug reservoir layer described above may be directly applied to the skin of a patient, and such embodiment is also included in the present invention.

Intermediate Membrane

The intermediate membrane of the present invention is placed on the side of skin of the drug reservoir layer. In consideration of the effective treatment of dementia and the reduction of the side effect of the drug, it is desirable to maintain the blood concentration of the antidementia drug in a proper range and thus it is preferred to maintain the variation of the flux of the percutaneous absorption preparation in a certain range. The intermediate membrane of the present invention is advantageously used for controlling the flux of a percutaneous absorption preparation within a certain range and obtaining a proper drug release profile.

The intermediate membrane of the present invention is not particularly limited as far as it can control the release of the antidementia drug to the adherent layer, and preferably a micro porous membrane having pores which allow permeation of the antidementia drug. In this case, the release of the drug by the membrane is controlled by the migration of the drug through the pores.

The material of the intermediate membrane may be selected from any porous materials which permit the permeation of the antidementia drug, and preferably the one selected from the group consisting of polypropylene, polyethylene, polyacrylonitrile, polytetrafluoroethylene, polydimethylsiloxane and polymethyl methacrylate, more preferably polypropylene.

The porosity, pore size and thickness of the intermediate membrane can be appropriately determined in consideration of the physicochemical properties such as the molecular weight of the antidementia drug, the flux required, and the like, and the intermediate membrane can be made, for example, to have a porosity in the range of ca. 10-85%, a pore size in the range of ca. 0.03-0.25 µm×µm, a thickness in the range of ca. 20-50 µm.

In this connection, the intermediate membrane, which may be a single layer, may also be a multi-layer having plural micro porous membranes laminated, and the present invention also includes such embodiment.

Adherent Layer

The adherent layer of the present invention is placed on the side of skin of the intermediate membrane. Thus, the drug reservoir layer and the adherent layer are separately placed in the percutaneous absorption preparation according to the present invention, which enables the adhesion of the adherent layer to be increased conspicuously and is advantageous to the administration of the antidementia drug for a long period.

The constituent material of the adherent layer of the present invention is not particularly limited as far as it allow the permeation of antidementia drug and can make the percutaneous absorption preparation attached to skin, and it is preferably an acrylic polymer. The addition of the acrylic polymer to the adherent layer is advantageous to the improvement of the adhesion of the adherent layer. Moreover, the acrylic polymer includes preferably the same one as the acrylic polymer in the drug reservoir layer.

In addition, the content of the acrylic polymer in the adherent layer is preferably in the range of 70-100% by weight, more preferably 80-95% by weight.

Also, the adherent layer further comprises an carboxylic acid ester. The carboxylic acid ester is preferably the same one as the acrylic polymer in the drug reservoir layer, which is selected from an ester of a polyvalent carboxylic acid and a monohydroxy alcohol, an ester of a fatty acid and a polyhydric alcohol, and a combination thereof.

The content of the carboxylic acid ester in the adherent layer is preferably in the range of 5-30% by weight, more preferably 5-20% by weight. When the ester of a polyvalent carboxylic acid and a monohydroxy alcohol is used, the content of the ester in the adherent layer is preferably in the range of 3-15% by weight, more preferably 3-10% by weight. Also, when the ester of a fatty acid and a polyhydric alcohol is used, the content of the ester in the adherent layer is preferably in the range of 1-10% by weight, more preferably 2-5% by weight.

The adherent layer of the present invention can be formed by appropriately combining the constituents and amounts thereof described above, provided that these constituents and the amounts thereof are used in the adherent layer.

According to the preferred embodiment of the present invention, the adherent layer comprises a (meth)acrylate-vinyl ester copolymer; an alkyl ctirate ester and/or an alkyl sebacate ester; and a sorbitan fatty acid ester.

Also, according to the more preferred embodiment of the present invention, the adherent layer comprises a copolymer composed of a monomer unit selected from a C1-12 alkyl (meth)acrylate, a monohydroxy C2-4 alkyl(meth)acrylate, a glycidyl(meth)acrylate, and a combination thereof and vinyl acetate; a C2-4 alkyl citrate and/or a C2-4 alkyl sebacate; and a sorbitan C7-19 fatty acid ester.

Furthermore, according to the more preferred embodiment of the present invention, the adherent layer comprises a copolymer composed of 2-ethylhexyl acrylate, hydroxyethyl acrylate, glycidyl methacrylate and vinyl acetate; a tri-(C2-4)-alkyl citrate and/or a di-(C2-4)-alkyl sebacate; and sorbitan C7-19 fatty acid ester.

Also, the thickness of the adherent layer of the present invention is appropriately determined by those skilled in the art, and can be in the range of 50-100 µm.

Combination of Layers and Membrane/flux

The percutaneous absorption preparation according to the present invention is a laminate of the drug reservoir layer, the intermediate membrane and the adherent layer as described above. The specific combination of the drug reservoir layer, the intermediate membrane and the adherent layer and the amount of the respective constituents are appropriately selected by those skilled in the art.

Further, according to the more preferred embodiment of the present invention, in the percutaneous absorption preparation, the drug reservoir layer comprises a basic antidementia drug or a salt thereof, an aminated polymer, a polyhydric alcohol, an ester of a polyvalent carboxylic acid and a monohydroxy alcohol, an ester of a fatty acid and a polyhydric alcohol, and an acrylic polymer, the intermediate membrane is a micro porous membrane having pores which allow permeation of the antidementia drug, and the adherent layer comprises an acrylic polymer, an ester of a polyvalent carboxylic acid and a monohydroxy alcohol and an ester of a fatty acid and a polyhydric alcohol.

Also, according to the further preferred embodiment of the present invention, in the percutaneous absorption preparation, the drug reservoir layer comprises the basic antidementia drug or a salt thereof; a methyl(meth)acrylate-butyl (meth)acrylate-dimethylaminoethyl(meth)acrylate copolymer; a sugar alcohol and/or a glycol; a C2-4 alkyl citrate and/or a C2-4 alkyl sebacate; a sorbitan C7-19 fatty acid ester; and a (meth)acrylic acid-vinyl ester copolymer, the intermediate membrane is a micro porous membrane having pores which allow permeation of the antidementia drug, and the adherent layer comprises a (meth)acrylic acid-vinyl ester copolymer; a C2-4 alkyl citrate and/or a C2-4 alkyl sebacate; and a sorbitan C7-19 fatty acid ester.

Also, according to the further preferred embodiment of the present invention, in the percutaneous absorption preparation, the drug reservoir layer comprises the basic antidementia drug or a salt thereof; a methyl(meth)acrylate-butyl (meth)acrylate-dimethylaminoethyl(meth)acrylate copolymer; a sugar alcohol and/or a glycol; a C2-4 alkyl citrate and/or a C2-4 alkyl sebacate; a sorbitan C7-19 fatty acid ester; and a copolymer composed of a monomer unit selected from a C1-12 alkyl (meth)acrylate, a monohydroxy C2-4 alkyl (meth)acrylate, a glycidyl(meth)acrylate, and a combination thereof, and vinyl acetate, the intermediate membrane is a micro porous membrane having pores which allow permeate of the antidementia drug, and the adherent layer comprises a copolymer composed of a monomer unit selected from a C1-12 alkyl(meth)acrylate, a monohydroxy C2-4 alkyl(meth)acrylate, a glycidyl(meth)acrylate, and a combination thereof, and vinyl acetate; a C2-4 alkyl citrate and/or a C2-4 alkyl sebacate; and a sorbitan C7-19 fatty acid ester.

Also, according to the further preferred embodiment of the present invention, in the percutaneous absorption preparation, the drug reservoir layer comprises the basic antidementia drug or a salt thereof; a methyl methacrylate-butyl methacrylate-dimethylaminoethyl methacrylate copolymer; at least one polyhydric alcohol selected from the group consisting of glycerin, propylene glycol, dipropylene glycol, butylene glycol, d-sorbitol, xylitol, mannitol and polyethylene glycol; a tri-(C2-4)-alkyl citrate and/or a di-(C2-4)-alkyl sebacate; a sorbitan C7-19 fatty acid ester; and a copolymer composed of 2-ethylhexyl acrylate, hydroxyethyl acrylate, glycidyl methacrylate and vinyl acetate, the intermediate membrane is a micro porous membrane having pores which allow permeation of the antidementia drug, and the adherent layer comprises a copolymer composed of 2-ethylhexyl acrylate, hydroxyethyl acrylate, glycidyl methacrylate and vinyl acetate; a tri-(C2-4)-alkyl citrate and/or a di-(C2-4)-alkyl sebacate; and a sorbitan C7-19 fatty acid ester.

It is also possible to place a stretchable or non-stretchable backing layer on one side of the drug reservoir layer in the percutaneous absorption preparation according to the present invention. The backing layer can be selected from, but is not limited to, for example woven fabric, nonwoven fabric, PET (polyethylene terephthalate), polyurethane, polyester, polyethylene, polyvinyl acetate, aluminum, and the like, or a composite material thereof.

A well known liner may be placed on the adhesive surface between the adherent layer and skin, and the liner is peeled off at the use of the preparation.

The application area of the percutaneous absorption preparation is appropriately controlled depending on factors such as the amount or flux of the drug, the condition of a patient, and it may be made in the range of ca. 5-100 cm$^2$.

It is also possible in the percutaneous absorption preparation according to the present invention to appropriately control the flux of the antidementia drug depending on the amounts of the drug and other constituents as well as the kinds of the intermediate membrane, and the like. However, in consideration of the administration of the antidementia drug for a long period, the maximal flux of the antidementia drug in the percutaneous absorption preparation is preferably in the range of 3 mcg/cm$^2$/hr or more, more preferably 3-6 mcg/cm$^2$/hr. Furthermore, it is preferred that the maximal flux is shown at and after 48 hours after plaster, more preferably at 72-120 hours after plaster. Moreover, the flux of the antidementia drug at the point of 168 hours after plaster is preferably 70% or more of the maximal flux of the antidementia drug after plaster, more preferably 70-90%.

Preparation Method

As the method for preparing the percutaneous absorption preparation according to the present invention, an adhesive mass solution obtained by mixing the constituent materials of the drug reservoir layer is first coated on the liner. Next, the adhesive mass solution is dried at a temperature of about 70-80° C. to obtain the drug reservoir layer, on which a backing layer is laminated. Next, an adhesive mass solution which is composed of the materials comprising the adherent layer is coated on a liner and dried at a temperature of about 70-80° C., on which the drug intermediate membrane is further laminated. The liner in the drug reservoir layer is then peeled off, and the drug reservoir layer can be laminated on a surface opposite to the adherent layer in the drug intermediate membrane to give the percutaneous absorption preparation according to the present invention.

To the adhesive mass solution used for the preparation of the drug reservoir layer and the adherent layer may be appropriately added an organic solvent in addition to the constituent materials of the solution. The organic solvent includes, for example, ethyl acetate, butyl acetate, toluene, n-hexane, tetrahydrofuran, dimethylformamide, methanol, ethanol, and the like.

Therapeutic Method

According to the percutaneous absorption preparation of the present invention, the sustaining percutaneous administration of the antidementia drug can be stably made, and it becomes possible to treat effectively dementia even in a patient with progressed symptom. Thus, according to another embodiment of the present invention, a method for treating dementia comprising plastering on the skin of a living body with the percutaneous absorption preparation.

The amount of the antidementia drug is appropriately determined by those skilled in the art depending on the kinds of drugs, the symptoms of patients, dosage periods, the sizes of preparations, and the like.

Also, the application period can be set in a long period even in the case of single dosage, preferably for 3-7 days, more preferably about 7 days.

Also, the living body described above includes, for example, rabbit, dog, or human, preferably human.

EXAMPLES

Example 1

Preparation of a Drug Reservoir Layer

EUDRAGIT® E100 (35.3 g) was dissolved in 45.9 g of ethyl acetate. To this solution were added 50 g of donepezil hydrochloride, 20 g of triethyl citrate, 20 g of glycerin and 10 g of sorbitan monolaurate, and the mixture was stirred. Next, 152.1 g of an acrylic polymer (DURO-TAK®387-2516, National Starch & Chemical Co., Ltd.)(solid content: 42.5%) was added to the solution to give an adhesive mass solution. The adhesive mass solution was coated on a polyethylene terephthalate liner so that the coat after drying had a thickness of 100 μm. Then, the adhesive mass solution on the liner was dried at 70° C. for 15 minutes to form a drug reservoir layer having the desired thickness. Furthermore, the drug reservoir layer was laminated on a backing layer (SCOTCH-PAK®9732, 3M).

Preparation of an Adherent Layer and a Percutaneous Absorption Preparation

Triethyl citrate (12 g), sorbitan monolaurate (6 g), and an acrylic polymer (DURO-TAK®387-2516, National Starch & Chemical) (239.9 g; solid content: 42.5%) were mixed by stirring. The adhesive mass solution obtained was coated on a polyethylene terephthalate liner so that the coat after drying had a thickness of 50 gm. Then, the adhesive mass solution on the liner was dried at 70° C. for 10 minutes to form an adherent layer having the desired thickness. A micro porous polypropylene membrane (CELGARD®2400, Celgard Inc.) was laminated on the adherent layer. The liner of the drug reservoir layer was peeled off and laminated on a surface opposite to the adherent layer in the micro porous polypropylene membrane to give a percutaneous absorption preparation shown in the section of FIG. 1.

In FIG. 1, the percutaneous absorption preparation 1 is composed of the backing layer 2, the drug reservoir layer 3, the intermediate membrane 4, and the adherent layer 5. Furthermore, the liner 6 is placed on one surface of the skin side of the adherent layer 5.

Example 2

A percutaneous absorption preparation was obtained by the similar manner to Example 1 with use of diethyl sebacate instead of triethyl citrate.

Example 3

Preparation of a Drug Reservoir Layer

A drug reservoir layer was formed by the similar manner to Example 1 except that a laminated material of woven fabric and PET was used as a backing layer and the drug reservoir layer was laminated on the PET side of the backing layer.

Preparation of an Adherent Layer and a Percutaneous Absorption Preparation

Triethyl citrate (12 g), sorbitan monolaurate (6 g), an acrylic polymer (DURO-TAK®87-2287, National Starch & Chemical)(201.98 g; solid content: 50.5%), and ethyl acetate (46.69 g) were mixed by stirring. The adhesive mass solution obtained was coated on a polyethylene terephthalate liner so that the coat after drying had a thickness of 50 μm. Then, the adhesive mass solution on the liner was dried at 70° C. for 10 minutes to form an adherent layer having the desired thickness. A micro porous polypropylene membrane (CELGARD®2400, Celgard Inc.) was laminated on the adherent layer.

The liner of the drug reservoir layer was further peeled off and laminated on a surface opposite to the adherent layer in the micro porous polypropylene membrane to give a percutaneous absorption preparation.

Test 1

In Vitro Human Skin Permeation Test

The Percutaneous Absorption Preparation (application area: 4.5 cm$^2$) obtained in Example 1 or 2 was plastered on a side of the corneal layer in human skin, and a flow-through-cell (5 cm$^2$) having warm water circulated therethrough so that the surface of the skin was kept at about 32° C. A phosphate buffered physiological saline solution (pH 7.4) was used as a receiver solution, of which portion was taken up at a rate of 5 ml/hr every 2 hours until 168 hours after plastering with the preparation. The amount of the drug in the sampling solution was determined by HPLC to estimate the permeation rate per hour and to determine the average flux per unit area (mcg/cm$^2$/hr). In this connection, each flux estimation is an average value at every two hours. Thus, the flux at the point of 168 hours after plaster ($J_{168}$) means the average of the flux at 166-168 hours after plaster.

As a result of the human skin permeation test, the average flux (mcg/cm$^2$/hr; n=3) changed as shown in FIG. 2. In addition, when the preparation in Example 1 or 2 was used, the time for arriving at the maximal flux, the maximal flux ($J_{max}$: mcg/cm$^2$/hr), the average flux at the point of 168 hours after plaster ($J_{168}$: mcg/cm$^2$/hr), and the flux at the point of 168 hours after plaster/maximal flux ($J_{168}$/J max; %) were as shown in Table 1.

TABLE 1

|  | Time for arriving at max. flux (hr) | Max. flux ($J_{max}$: mcg/cm$^2$/hr) | Flux at 168 hours after plaster ($J_{168}$: mcg/cm$^2$/hr) | $J_{168}$/$J_{max}$ (%) |
|---|---|---|---|---|
| Example 1 | 79 | 3.92 | 3.10 | 79.08 |
| Example 2 | 73 | 4.06 | 3.24 | 79.80 |

Test Example 2

In Vivo Test for Measuring the Rabbit Blood Concentration of Drug

A sheet of the percutaneous absorption preparation (35 cm$^2$) in Example 1 or 2 was plastered on the back of rabbits (male, 10 weeks, n=6) of which back was shaved. and peeled off at 168 hours after plastering. Blood was sampled at the time of 2, 4, 8, 12, 24, 48, 72, 96, 120, 144, 168, 170, 172, 174 and 176 hours after plastering. The plasma concentration of donepezil obtained was measured by LC/MS/MS.

The variation of the average of the measured plasma concentration of donepezil was as shown in FIG. 3. The plasma concentration of donepezil was maintained at a level of 10 ng/ml or more for a period of 24-168 hours after plaster.

Test Example 3

In Vivo Test for Measuring the Dog Blood Concentration of Drug

A sheet of the percutaneous absorption preparation (35 cm$^2$) in Example 3 was plastered on the abdomen of dogs (male, beagle, n=8) of which abdomen was shaved, and peeled off at 168 hours after plaster. Blood was sampled at the time of 2, 4, 6, 12, 24, 36, 48, 60, 72, 84, 96, 108, 120, 132, 144, 156 and 168, and the plasma concentration of donepezil obtained was measured by LC/MS/MS.

Also, an oral preparation (Aricept® tablet, Eisai Co., Ltd., 2×5 mg tablet) was singly administered per os with 10 ml of water to dogs (male, beagle, n=8) which have been fasted for 24 hours. Blood was taken up at the time of 0.5, 1, 2, 3, 4, 6, 8, 12 and 24 hours after the administration, and the plasma concentrations of donepezil obtained were measured by LC/MS/MS.

Figure 4:
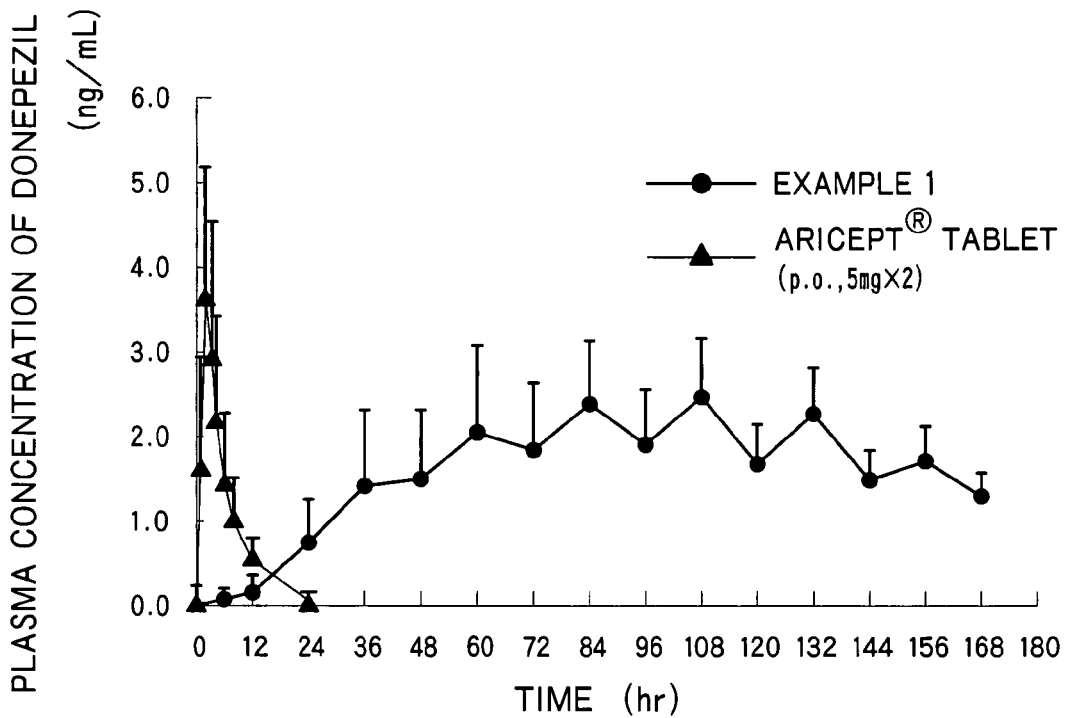
FIG. 4 is a graph which shows the concentration of the antidementia drug in dog plasma in a single dosage of the percutaneous absorption preparation according to the present invention.

As regards the percutaneous absorption preparation in Example 3 and the oral preparation described above, the variation of the plasma concentration of donepezil (average±SD) was as shown in FIG. 4. The plasma concentration of donepezil was maintained at a level of 1.0 ng/ml or more for a period of 48-168 hours after plaster.

What is claimed is:

1. A percutaneous absorption preparation of donepezil used as a plaster to skin, which comprises at least an adherent layer, an intermediate membrane, and a drug reservoir layer sequentially from the side which is plastered on skin, wherein
said drug reservoir layer comprises donepezil or a salt thereof; a dialkylaminoalkyl (meth)acrylate-alkyl (meth)acrylate copolymer; a polyhydric alcohol selected from a sugar alcohol and a glycol; a carboxylic acid ester selected from an alkyl citrate ester and an alkyl sebacate ester; a sorbitan fatty acid ester; and a (meth) acrylate-vinyl ester copolymer, said intermediate membrane is a microporous membrane having pores which allow permeation of donepezil, and said adherent layer enables the plastering of the percutaneous absorption preparation to skin, is permeable to donepezil, and comprises a carboxylic acid ester selected from an alkyl citrate ester and an alkyl sebacate ester; a sorbitan fatty acid ester; and a (meth)acrylate-vinyl ester copolymer.

2. A percutaneous absorption preparation according to claim 1, wherein the content of donepezil or a salt thereof in said drug reservoir layer is in the range of 10-40% by weight.

3. A percutaneous absorption preparation according to claim 1, wherein said dialkylaminoalkyl (meth)acrylate-alkyl (meth)acrylate copolymer is a methyl (meth)acrylate-butyl (meth)acrylate-dimethylaminoethyl (meth)acrylate copolymer.

4. A percutaneous absorption preparation according to claim 1, wherein said polyhydric alcohol is at least one selected from the group consisting of glycerin, propylene glycol, dipropylene glycol, butylene glycol and polyethylene glycol.

5. A percutaneous absorption preparation according to claim 1, wherein said intermediate membrane is composed of a material selected from the group consisting of polypropylene, polyethylene, polyacrylonitrile, polytetrafluoroethylene, polydimethylsiloxane and polymethyl methacrylate.

6. A percutaneous absorption preparation according to claim 1, wherein the maximal skin permeation rate of donepezil after plaster is 3 mcg/cm$^2$/hr or more.

7. A percutaneous absorption preparation according to claim 1, wherein the skin permeation rate of donepezil at the point of 168 hours after plaster is 70% or more of the maximal skin permeation rate of donepezil after plaster.

8. A method for the treatment of dementia, comprising plastering the skin of a living body with the percutaneous absorption preparation according to claim 1.

* * * * *